US010939866B2

(12) United States Patent
Tsoneva et al.

(10) Patent No.: US 10,939,866 B2
(45) Date of Patent: Mar. 9, 2021

(54) SYSTEM AND METHOD FOR DETERMINING SLEEP ONSET LATENCY

(71) Applicant: KONINKLIJKE PHILIPS N.V., Eindhoven (NL)

(72) Inventors: Tsvetomira Kirova Tsoneva, Eindhoven (NL); Gary Nelson Garcia Molina, Madison, WI (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 204 days.

(21) Appl. No.: 16/205,330

(22) Filed: Nov. 30, 2018

(65) Prior Publication Data

US 2019/0192068 A1    Jun. 27, 2019

Related U.S. Application Data

(60) Provisional application No. 62/597,460, filed on Dec. 12, 2017.

(51) Int. Cl.
| | |
|---|---|
| *A61B 5/00* | (2006.01) |
| *A61B 5/048* | (2006.01) |
| *A61B 5/11* | (2006.01) |
| *A61M 21/00* | (2006.01) |
| *A61M 21/02* | (2006.01) |
| *A61B 5/0476* | (2006.01) |

(52) U.S. Cl.
CPC ............ *A61B 5/4809* (2013.01); *A61B 5/048* (2013.01); *A61B 5/0476* (2013.01); *A61B 5/1103* (2013.01); *A61B 5/4812* (2013.01); *A61B 5/6804* (2013.01); *A61M 21/00* (2013.01); *A61M 21/02* (2013.01); *A61B 5/4836* (2013.01); *A61M 2021/0016* (2013.01);
(Continued)

(58) Field of Classification Search
CPC .......... A61M 21/02; A61M 2205/3313; A61B 5/4809; A61B 5/4812
See application file for complete search history.

(56) References Cited

U.S. PATENT DOCUMENTS

| | | | |
|---|---|---|---|
| 10,137,276 | B2 | 11/2018 | Garcia Molina et al. |
| 2001/0028309 | A1 | 10/2001 | Torch |

(Continued)

FOREIGN PATENT DOCUMENTS

WO    2018115277 A1    6/2018

OTHER PUBLICATIONS

International Search Report and Written Opinion, International Application No. PCT/EP2018/084071, dated Apr. 8, 2019.
(Continued)

*Primary Examiner* — Christine H Matthews

(57) ABSTRACT

The present disclosure pertains to a system and method for determining sleep onset latency in a subject. The system is configured to generate output signals conveying information related to brain activity in the subject, determine sleep stages of the subject based on the output signals, determine a sleep onset moment in the subject based on the determined sleep stages, determine a sleep intention moment for the subject by: (i) detecting eye blinks in the subject based on the output signals, and determining the sleep intention moment responsive to the detected eye blinks ceasing for a predetermined period of time; and/or (ii) determining whether brain activity power in a target frequency band has breached a threshold power level based on the output signals, and determining the sleep intention moment responsive to a breach; and determine the sleep onset latency based on the sleep onset moment and the sleep intention moment.

12 Claims, 5 Drawing Sheets

(52) U.S. Cl.
CPC ............ *A61M 2021/0022* (2013.01); *A61M 2021/0027* (2013.01); *A61M 2021/0044* (2013.01); *A61M 2021/0055* (2013.01); *A61M 2021/0072* (2013.01); *A61M 2205/3313* (2013.01); *A61M 2205/3375* (2013.01); *A61M 2205/3553* (2013.01); *A61M 2205/3561* (2013.01); *A61M 2205/3569* (2013.01); *A61M 2205/3584* (2013.01); *A61M 2205/3592* (2013.01); *A61M 2205/502* (2013.01); *A61M 2209/088* (2013.01); *A61M 2210/06* (2013.01); *A61M 2230/04* (2013.01); *A61M 2230/10* (2013.01); *A61M 2230/14* (2013.01); *A61M 2230/20* (2013.01); *A61M 2230/40* (2013.01); *A61M 2230/50* (2013.01); *A61M 2230/63* (2013.01)

(56) References Cited

U.S. PATENT DOCUMENTS

| | | |
|---|---|---|
| 2007/0267439 A1 | 11/2007 | Farzan |
| 2015/0306391 A1 | 10/2015 | Wu et al. |
| 2016/0045706 A1 | 2/2016 | Garcia Molina et al. |
| 2016/0082222 A1 | 3/2016 | Garcia Molina et al. |
| 2016/0296164 A1 | 10/2016 | Garcia Molina |
| 2016/0302718 A1 | 10/2016 | Laura Lapoint et al. |

OTHER PUBLICATIONS

"Sleep onset latency", https://en.wikipedia.org/wiki/Sleep_onset_latency, last edited Mar. 2018.

Kräuchi, K., Cajochen, C., Werth, E., & Wirz-Justice, A. (2000). Functional link between distal vasodilation and sleep-onset latency?. American Journal of Physiology—Regulatory, Integrative and Comparative Physiology, 278(3), R741-R748.

Haynes, S. N., Adams, A., & Franzen, M. (1981). The effects of presleep stress on sleep-onset insomnia. Journal of Abnormal Psychology, 90(6), 601.

Reid, K., Van Den Heuvel, C. A. M. E. R. O. N., & Dawson, D. (1996). Day-time melatonin administration: effects on core temperature and sleep onset latency. Journal of sleep research, 5(3), 150-154.

Richardson, G. S., Carskadon, M. A., Flagg, W., Van den Hoed, J., Dement, W. C., & Mitler, M. M. (1978). Excessive daytime sleepiness in man: multiple sleep latency measurement in narcoleptic and control subjects. Electroencephalography and clinical neurophysiology, 45(5), 621-627.

Abo-Zahhad, M., Ahmed, S. M., & Abbas, S. N. (2015). A new EEG acquisition protocol for biometric identification using eye blinking signals. International Journal of Intelligent Systems and Applications, 7(6), 48.

Ohayon, M. M., Carskadon, M. A., Guilleminault, C., & Vitiello, M. V. (2004). Meta-analysis of quantitative sleep parameters from childhood to old age in healthy individuals: developing normative sleep values across the human lifespan. Sleep—New York Then Westchester-, 27, 1255-1274.

Frey, Jeremy, "OpenBCI crossing swords with motor imagery", Mar. 2015, http://openbci.com/community/openbci-crossing-swords-with-motor-imagery/.

Kaida, K., Takahashi, M., Åkerstedt, T., Nakata, A., Otsuka, Y., Haratani, T., & Fukasawa, K. (2006). Validation of the Karolinska sleepiness scale against performance and EEG variables. Clinical Neurophysiology, 117(7), 1574-1581.

SYSTEM AND METHOD FOR DETERMINING SLEEP ONSET LATENCY

CROSS-REFERENCE TO PRIOR APPLICATIONS

This application claims the benefit of U.S. Provisional Application No. 62/597,460, filed on 12 Dec. 2017. This application is hereby incorporated by reference herein.

BACKGROUND

1. Field

The present disclosure pertains to a system and method for determining sleep onset latency in a subject for a sleep session.

2. Description of the Related Art

Sleep monitoring and sleep onset latency determination systems are frequently used to identify sleep disorders or in connection with sleep therapy. Typical systems may continually measure physical movement of a subject and detect environmental light levels (e.g., to determine when the subject has turned off the lights) to assess when the subject actually intends to sleep and when sleep onset begins. Such systems, however, often fail to accurately assess sleep onset latency, for example, due to changes in the subject's intentions (e.g., deciding to get up, to operate a mobile phone, etc.) that may fail to be detected by subject movement measurements, light exposure measurements, or other common techniques.

SUMMARY

Accordingly, one or more aspects of the present disclosure relate to a system configured to determine sleep onset latency for a subject for a sleep session. The system comprises one or more sensors, one or more hardware processors, and/or other components. The sensors are configured to generate output signals conveying information related to brain activity in the subject during the sleep session. The hardware processors are operatively coupled with the sensors and/or other components. The hardware processors are configured by machine-readable instructions. The hardware processors are configured to determine one or more sleep stages of the subject based on the output signals. The sleep stages indicate presence of sleep in the subject during the sleep session. The hardware processors are configured to determine a sleep onset moment in the subject based on the determined sleep stages. The sleep onset moment comprises a moment in time indicating a start of sleep in the subject during the sleep session. The hardware processors are configured to determine a sleep intention moment for the subject. The sleep intention moment comprises a moment in time indicating an intention of the subject to initiate sleep. The sleep intention moment is determined based on the output signals. As an example, the sleep intention moment is determined by: (i) detecting eye blinks in the subject based on the output signals, and determining the sleep intention moment responsive to the detected eye blinks ceasing for a predetermined period of time; or (ii) determining whether brain activity power in a target frequency band has breached a threshold power level based on the output signals, and determining the sleep intention moment responsive to a breach; or (iii) a combination of (i) and (ii). The hardware processors are configured to determine the sleep onset latency based on the sleep onset moment and the sleep intention moment.

Yet another aspect of the present disclosure relates to a method for determining sleep onset latency for a subject for a sleep session with a determination system. The system comprises one or more sensors, one or more hardware processors, and/or other components. The method comprises generating, with the sensors, output signals conveying information related to brain activity in the subject during the sleep session. The method comprises determining, with the hardware processors, one or more sleep stages of the subject based on the output signals. The sleep stages indicate presence of sleep in the subject during the sleep session. The method comprises determining, with the hardware processors, a sleep onset moment in the subject based on the determined sleep stages. The sleep onset moment comprises a moment in time indicating a start of sleep in the subject during the sleep session. The method comprises determining, with the hardware processors, a sleep intention moment for the subject. The sleep intention moment comprises a moment in time indicating an intention of the subject to initiate sleep. The sleep intention moment is determined based on the output signals. As an example, the sleep intention moment is determined by: (i) detecting eye blinks in the subject based on the output signals, and determining the sleep intention moment responsive to the detected eye blinks ceasing for a predetermined period of time; or (ii) determining whether brain activity power in a target frequency band has breached a threshold power level based on the output signals, and determining the sleep intention moment responsive to a breach; or (iii) a combination of (i) and (ii). The method comprises determining, with the hardware processors, the sleep onset latency based on the sleep onset moment and the sleep intention moment.

Still another aspect of present disclosure relates to a system for determining sleep onset latency for a subject for a sleep session. The system comprises means for generating output signals conveying information related to brain activity in the subject during the sleep session. The system comprises means for determining one or more sleep stages of the subject based on the output signals. The sleep stages indicate presence of sleep in the subject during the sleep session. The system comprises means for determining a sleep onset moment in the subject based on the determined sleep stages. The sleep onset moment comprises a moment in time indicating a start of sleep in the subject during the sleep session. The system comprises means for determining a sleep intention moment for the subject. The sleep intention moment comprises a moment in time indicating an intention of the subject to initiate sleep. The sleep intention moment is determined based on the output signals. As an example, the sleep intention moment is determined by: (i) detecting eye blinks in the subject based on the output signals, and determining the sleep intention moment responsive to the detected eye blinks ceasing for a predetermined period of time; or (ii) determining whether brain activity power in a target frequency band has breached a threshold power level based on the output signals, and determining the sleep intention moment responsive to a breach; or (iii) a combination of (i) and (ii). The system comprises means for determining the sleep onset latency based on the sleep onset moment and the sleep intention moment.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
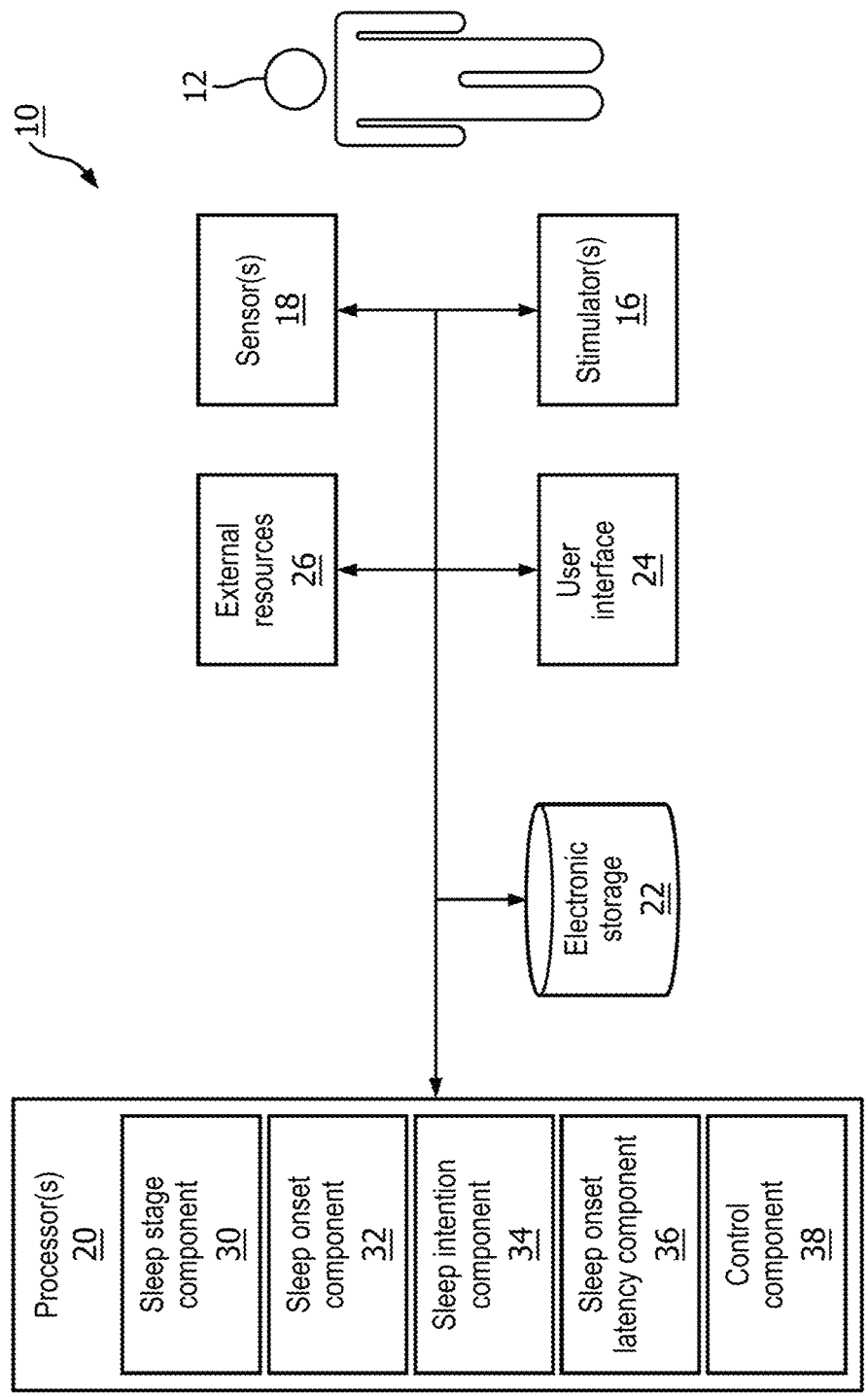
FIG. 1 is a schematic illustration of a system configured to determine sleep onset latency for a subject for a sleep session, in accordance with one or more embodiments.

As used herein, the singular form of "a", "an", and "the" include plural references unless the context clearly dictates otherwise. As used herein, the term "or" means "and/or" unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 is a schematic illustration of a system 10 configured to determine sleep onset latency for a subject 12 for a sleep session. In some embodiments, sleep onset latency is the time it takes to actually fall asleep once one has decided to initiate sleep (sleep intention). Sleep onset latency is the length of time that it takes for the transition from full wakefulness to sleep to occur. Sleep onset latency is often used as a biomarker for sleepiness and in diagnostics of insomnia. It is also part of the determination of sleep efficiency (e.g., the percentage of time asleep out of total time in bed) and total sleep time (e.g., the duration of sleep). Normal sleep onset latency is often between 13 and 19 minutes for adults between the ages of 20 and 50. Significant variation in these numbers is often an indication of a sleep disorder. For example, longer latencies are associated with sleep onset insomnia, which is a condition describing chronic difficulty falling asleep. Shorter latencies are associated with extreme sleepiness (e.g., during the daytime) which may be a result of insufficient sleep, sleep deprivation, and/or narcolepsy.

Clinical sleep studies and consumer sleep assessment devices provide sleep onset latency estimates. Prior sleep onset latency estimation approaches and/or systems are limited by their inconsistency in defining sleep intention and sleep onset. For example, in clinical settings, sleep intention is imposed by turning the lights off, but this event does not necessarily reflect sleep intention of a subject (e.g., a subject may simply lie in bed awake with the lights off).

In home settings, sleep onset may be detected as a long period of quiescence (e.g., using actigraphy based detection methods), while sleep intention is often explicitly obtained from users via entries and/or selections made via user interfaces in prior art systems. Inaccurate sleep onset latency estimates in these prior art systems limit the diagnostic accuracy of such systems to detect sleep disorders and may mislead users of consumer sleep monitoring devices. For example, consumer devices configured to monitor sleep at home offer opportunities for both users and clinicians to obtain objective estimations of sleep parameters over time. However, existing devices often create the wrong idea of sleep problems where there are none and, in turn, trigger sleep problems such as anxiety and insomnia. At home, sleep intention is difficult to estimate because users are often involved in various bedtime activities that require little to no movement such as reading books, watching television, or using their phones, which can all result in an incorrect estimation (e.g., too long) of sleep onset latency.

Typical sleep is characterized by sleep stages which occur in a cyclic manner (sleep cycles) and have different contributions to the restorative value of sleep. System 10 is configured to identify sleep stages using polysomnography (PSG) and/or other methods (as described below). Stage 1 and 2 are stages of light sleep, characterized by theta (4-8 Hz) oscillatory brain activity, and sleep spindles and K-complexes respectively. Stages 3 and 4 are stages of deep sleep characterized by slow-waves and delta activity (0.5-4 Hz) (described below). Rapid eye movement (REM) sleep typically occurs after around 90 minutes of sleep onset and is characterized by increased eye movement, hearth rate, and respiration rate. System 10 is configured such that sleep onset (SO) is determined to be the beginning of the first sleep state detected after sleep intention has been detected. In normal adult sleep, the first sleep state after wakefulness coincides with the lightest (e.g., stage 1) of the non-REM (NREM) sleep stages. In some embodiments, sleep onset is determined to be the beginning of any sleep stage detected for a predetermined period (e.g., 1 min and/or other times). Initiating sleep by REM can occur and is often indicative of a sleep disorder (e.g. narcolepsy). System 10 is configured such that sleep onset latency (SOL) is determined as a difference between the time of sleep onset and the time subject 12 intends to initiate sleep (SI). This is described by Equation 1 (Eq. 1) shown below.

$$SOL = SO - SI \qquad \text{(Eq. 1)}$$

System 10 uses an electroencephalogram (EEG) and/or other information determined based on sensor output signals to determine sleep onset latency. In some embodiments, sleep onset latency is determined based on the detection of sleep intention and sleep onset via EEG patterns. These patterns indicate eye blink extinction, alpha extinction, delta power, spindles, and/or other information related to sleep intention and/or sleep onset. Consistently providing accurate sleep onset latency determinations improves clinical accuracy and enhances consumer product credibility.

In some embodiments, system 10 includes one or more of a stimulator 16, a sensor 18, a processor 20, electronic storage 22, a user interface 24, external resources 26, and/or other components.

Sensor 18 is configured to generate output signals conveying information related to brain activity and/or other activity in subject 12. In some embodiments, brain activity includes any activity or lack of activity related to sleep and/or other activity in system 10. For example, sensor 18 may be a non-EEG sensor where system 10 is configured to detect sleep onset based on information from actigraphy sensors, cameras, and/or other sensors 18, and/or blink extinction from the camera information. This is further described below. In some embodiments, sensor 18 is configured to generate output signals conveying information related to slow wave activity (SWA) in subject 12. In some embodiments, the information related to brain activity and/or other activity in subject 12 is the information related to SWA. In some embodiments, sensor 18 can be any EEG, actigraphy, heart rate sensor, and/or any other sensor which can provide information related to any marker associated with sleep. SWA, for example, is not crucial for the system described herein. In some embodiments, sensor 18 is configured to generate output signals conveying information related to stimulation provided to subject 12 during sleep sessions.

In some embodiments, the sleep, SWA, and/or other brain activity of subject 12 may be used to detect sleep stages of subject 12. As described above, the sleep stage of subject 12 may be associated with rapid eye movement (REM) sleep or non-rapid eye movement (NREM) sleep. The sleep stage of subject 12 may be one or more of NREM stage N1, stage N2, or stage N3, REM sleep, and/or other sleep stages. In some embodiments, the sleep stage of subject 12 may be one or more of stage S1, S2, S3, or S4 (e.g., S1-S4 correspond to former sleep stage denominations, while N1, N2, and N3 correspond to the latest denominations). In some embodiments, NREM stage 2 and/or 3 (and/or S3 and/or S4) may be slow wave (e.g., deep) sleep. Sensor 18 may comprise one or more sensors that measure such parameters directly. For example, sensor 18 may include electroencephalogram (EEG) electrodes configured to detect electrical activity along the scalp of subject 12 resulting from current flows within the brain of subject 12. Sensor 18 may comprise one or more sensors that generate output signals conveying information related to SWA of subject 12 indirectly. For example, one or more sensors 18 may comprise a heart rate sensor that generates an output based on a heart rate of subject 12 (e.g., sensor 18 may be a heart rate sensor than can be located on the chest of subject 12 and/or a heart rate sensor comprising a camera configured to detect heart rate from a distance away from subject 12, and/or be configured as a bracelet on a wrist of subject 12, and/or be located on another limb of subject 12), movement of subject 12 (e.g., sensor 18 may comprise an accelerometer that can be carried on a wearable, such as a bracelet around the wrist and/or ankle of subject 12 such that sleep may be analyzed using actigraphy signals; a pressure sensor configured to detect changes in pressure on a bed and/or mattress (e.g., the pressure sensor could be placed under the bed/mattress/sheets/etc.), for example, that indicate movement of subject 12; and/or other movement sensors), respiration of subject 12, and/or other characteristics of subject 12.

In some embodiments, sensor 18 may comprise one or more of EEG electrodes, an electrooculogram (EOG) electrode, an actigraphy sensor, an electrocardiogram (EKG) electrode, a respiration sensor, a pressure sensor, a vital signs camera, a photoplethysmogram (PPG) sensor, a functional near infra-red sensor (fNIR), a temperature sensor, a microphone and/or other sensors configured to generate output signals related to (e.g., the quantity, frequency, intensity, and/or other characteristics of) stimulation provided to subject 12, and/or other sensors. Although sensor 18 is illustrated at a single location near subject 12, this is not intended to be limiting. Sensor 18 may include sensors disposed in a plurality of locations, such as for example, within (or in communication with) sensory stimulator 16, coupled (in a removable manner) with clothing of subject 12, worn by subject 12 (e.g., as a headband, wristband, etc.), positioned to point at subject 12 while subject 12 sleeps (e.g., a camera that conveys output signals related to movement of subject 12), coupled with a bed and/or other furniture where subject 12 is sleeping, and/or in other locations. In some embodiments, sensor 18 is configured to generate the output signals at predetermined times (e.g., intervals), substantially continuously, and/or at other times.

Processor 20 is configured to provide information processing capabilities in system 10. As such, processor 20 may comprise one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some embodiments, processor 20 may comprise a plurality of processing units. These processing units may be physically located within the same device (e.g., sensory stimulator 16, user interface 24, a server that is part of external resources 26, etc.), or processor 20 may represent processing functionality of a plurality of devices operating in coordination. In some embodiments, processor 20 may be and/or be included in a computing device such as a desktop computer, a laptop computer, a smartphone, a tablet computer, a server, and/or other computing devices. Such computing devices may run one or more electronic applications having graphical user interfaces configured to facilitate user interaction with system 10.

As shown in FIG. 1, processor 20 is configured to execute one or more computer program components. The computer program components may comprise software programs and/or algorithms coded and/or otherwise embedded in processor 20, for example. The computer program components may comprise one or more of a sleep stage component 30, a sleep onset component 32, a sleep intention component 34, a sleep onset latency component 36, a control component 38, and/or other components. Processor 20 may be configured to execute components 30, 32, 34, 36, and/or 38 by software; hardware; firmware; some combination of software, hardware, and/or firmware; and/or other mechanisms for configuring processing capabilities on processor 20.

It should be appreciated that although components 30, 32, 34, 36, and 38 are illustrated in FIG. 1 as being co-located within a single processing unit, in embodiments in which processor 20 comprises multiple processing units, one or more of components 30, 32, 34, 36, and/or 38 may be located remotely from the other components. The description of the functionality provided by the different components 30, 32, 34, 36, and/or 38 described below is for illustrative purposes, and is not intended to be limiting, as any of components 30, 32, 34, 36, and/or 38 may provide more or less functionality than is described. For example, one or more of components 30, 32, 34, 36, and/or 38 may be eliminated, and some or all of its functionality may be provided by other components 30, 32, 34, 36, and/or 38. As another example, processor 20 may be configured to execute one or more additional components that may perform some or all of the functionality attributed below to one of components 30, 32, 34, 36, and/or 38.

In some embodiments, sleep stage component 30 is configured to determine sleep stages of subject 12. The sleep stages indicate presence of sleep, depth of sleep, and/or other characteristics of subject 12 during the sleep session. In some embodiments, sleep stage component 30 is configured such that determining the sleep stages of subject 12 includes determining one or more brain activity parameters for subject 12. The brain activity parameters are determined based on the output signals and/or other information. In some embodiments, determining one or more brain activity parameters may include generating and/or monitoring an EEG during a sleep session of subject 12. The EEG may be displayed, for example, by user interface 24. In some embodiments, sleep stage component 30 is configured such that the brain activity parameters are and/or are related to a frequency, amplitude, phase, presence of specific sleep patterns such as spindles, K-complexes, or sleep slow waves, alpha waves, and/or other characteristics of an EEG signal. In some embodiments, the brain activity parameters are determined based on the frequency, amplitude, and/or other characteristics of the EEG signal. In some embodiments, the determined brain activity parameters and/or the characteristics of the EEG may be and/or indicate sleep stages that correspond to the REM and/or NREM sleep stages described above.

For example, typical EEG characteristics during NREM sleep include a transition from alpha waves (e.g., about 8-13 Hz) to theta waves (e.g., about 4-7 Hz) for sleep stage N1; presence of sleep spindles (e.g., about 11 to 16 Hz) and/or K-complexes (e.g., similar to sleep slow waves) for sleep stage N2; presence of delta waves (e.g., about 0.5 to 4 Hz), also known as sleep slow waves, with peak-to-peak amplitudes greater than about 75 uV for sleep stage N3; presence of light sleep and/or arousals, and/or other characteristics. In some embodiments, light sleep may be characterized by the fact that the alpha activity (e.g., EEG power in the 8-13 Hz band) is no longer present and slow waves are not present. In some embodiments, SWA is a continuous value (e.g., EEG power in the 0.4 to 4 Hz band), which is positive. System 10 may be configured to detect its absence by comparing the SWA in subject 12 to a threshold. In some embodiments, an absence of slow waves is indicative of light sleep. In addition, spindle activity (EEG power in the 11 to 16 Hz band) may be high. Deep sleep may be characterized by the fact that delta activity (e.g., EEG power in the 0.5 to 4 Hz band) is dominant. In some embodiments, EEG power in the delta band and SWA are the same with respect to sleep EEG. In some embodiments, sleep stage component 30 is configured to determine a change in an EEG delta power level caused by stimulation, a quantity of micro arousals in subject 12, other EEG power levels, and/or other parameters. In some embodiments, sleep stage component 30 is configured to determine a level of slow wave activity in subject 12, detect slow wave events, detect N1, N2, and/or N3 sleep, and/or determine other information. In some embodiments, sleep stage component 30 is configured to determine a type of (e.g., NREM) sleep by, for example, determining EEG power in the 0.5 to 4 Hz frequency band, which indicates SWA, and quantifying a density of slow waves in the EEG signal. In some embodiments, slow waves may not be present throughout the whole N3 period, for example, but it may be significantly more likely that such slow waves are present during N3. Slow waves may also be present (although to a lesser extent) during N2, for example.

In some embodiments, sleep stage component 30 is configured to determine a first sleep stage of subject 12. A first sleep stage often coincides with NREM sleep which can be detected by testing whether alpha, beta (or both) power are below pre-defined thresholds. A first sleep stage can, in abnormal sleep cases, coincide with REM sleep which can be detected by testing that the theta/alpha ratio exceeds pre-defined thresholds. Threshold based detection is one of many possible strategies to detect sleep. It should also be noted that more sophisticated (e.g. neural networks, non-linear support vector machines) machine learning algorithms can be used for sleep staging and/or for other purposes.

In some embodiments, sleep stage component 30 is configured to determine the sleep stages, the sleep and/or brain activity parameters described above, and/or other parameters at predetermined times (e.g., intervals), substantially continuously, and/or at other times. In some embodiments, brain activity parameters may be determined based on the EEG signals, electrocardiogram (ECG) signals, actigraphy signals, body temperature signals, galvanic skin response (GSR) signals, and/or other information related to the brain, the central and/or peripheral nervous systems of subject 12, and/or other biological systems of subject 12.

In some embodiments, sleep stage component 30 is configured to determine sleep stages (e.g., N1, N2, N3) while subject 12 is sleeping and/or before or after a sleep session. Sleep stage component 30 is configured to identify sleep stages based on the output signals from sensor 18, the parameters determined as described above, and/or other information. For example, sleep stage component 30 may identify sleep stages based on the SWA in subject 12, based on the hypnogram generated by sleep stage component 30, and/or other information.

Sleep onset component 32 is configured to determine a sleep onset moment of subject 12. The sleep onset moment comprises a moment in time indicating a start of sleep in subject 12 during the sleep session. In some embodiments, the sleep onset moment is the beginning of the first episode of sleep (e.g., stage 1, stage 2, etc.) that lasts longer than a predefined time (e.g., 30 seconds, but this is not intended to be limiting). Sleep onset component 32 is configured to determine the sleep onset moment based on the information in the output signals from sensor 18, the information determined by sleep stage component 30, and/or other information. For example, in some embodiments, sleep onset component 32 is configured to determine the sleep onset moment based on a hypnogram generated by sleep stage component 30 and/or other information. In some embodiments, determining the sleep onset moment in subject 12 comprises determining whether subject 12 has spent a predetermined amount of time in a predetermined sleep stage, and responsive to subject 12 spending the predetermined amount of time in the predetermined sleep stage, determining the sleep onset moment as a starting time of the predetermined amount of time in the predetermined sleep stage. For example, sleep onset component 32 may identify a substantially horizontal line in a hypnogram as an indication that subject 12 is in a specific sleep stage. The length of that horizontal line may indicate the amount of time subject 12 has spent in that sleep stage.

Sleep intention component 34 is configured to determine a sleep intention moment for subject 12. The sleep intention moment comprises a moment in time indicating an intention of subject 12 to initiate sleep. In some embodiments, the sleep intention moment is the moment when subject 12 closes his or her eyes, intending to go to sleep. In some embodiments, the sleep intention moment is the end of a first continuous epoch of a predefined duration (e.g., 30 seconds but this is not intended to be limiting) with the eyes of subject 12 closed before sleep onset. Sleep intention component 34 is configured to determine the sleep intention moment based on the information in the output signals from sensor 18, the information determined by sleep stage component 30, and/or other information. System 10 is configured such that brain activity related to the eyes of subject 12 is manifested in and/or determined based on (e.g., by sleep stage component 30 and/or sleep intention component 34) the information in the output signals (e.g., in the EEG and/or other information in and/or determined based the information in the output signals from sensor 18). For example, elevated alpha power is associated with a lack of stimuli and the idling of brain areas related to visual processing. Some of this activity, such as brain activity related to eye blinks, is considered an unwanted artifact and filtered from sensor output signals in prior art systems.

The presence of eye blinks indicates wakefulness in subject 12 (e.g., a lack of intention to fall asleep). Sleep intention component 34 is configured such that the sleep intention moment is determined by: (i) detecting eye blinks in the subject based on the output signals, and determining the sleep intention moment responsive to the detected eye blinks ceasing for a predetermined period of time; (ii) determining whether brain activity power in a target frequency band has breached a threshold power level based on the output signals, and determining the sleep intention moment responsive to a breach; (iii) a combination of (i) and (ii); and/or by other methods.

Eye blinks are physiological events that manifest in EEG, EOG, and/or other signals (e.g., output signals from sensor 18 and/or signals determined based on the information in the output signals from sensor 18). In some embodiments, detecting eye blinks in subject 12 comprises detecting a negative going zero crossing to a negative peak for a voltage of the output signals, followed by a positive going zero crossing and a positive peak, with a peak to peak distance within a distance threshold range and a peak to peak amplitude within an amplitude threshold range (further described below with respect to FIG. 2). In some embodiments, the peak to peak distance threshold range is about 100 to 500 milliseconds and/or other ranges. In some embodiments, the peak to peak amplitude threshold range is about 100 or more microvolts and/or other ranges. In some embodiments, eye blinks can also be detected considering the first derivative of the signal which informs on the slope and location of extreme points. Eye blinks can also be detected using machine learning algorithms which also extract features to optimize detection (e.g. deep neural networks). In some embodiments, system 10 is configured such that eye blinks are detected with a camera and/or EOG/EMG sensors attached to the face of subject 12. In some embodiments, given more than one sensor is distributed over the head of subject 12, system 10 is configured such that eye blinks are detected using linear decomposition, such as independent component analysis. In this procedure independent component filters are chosen to produce the maximally temporally independent signals available in the EEG data. The blink-related signal is then identified as the component which shows activity mainly in the front of the head. By inverse transformation, one can get back to time series data and identify the moment blinks cease.

In some embodiments, with respect to determining whether the brain activity power in the target frequency band has breached the threshold power level, the power is the alpha power, the target frequency band is the 8-13 Hz frequency band, the threshold power level is an average alpha power level; and a breach is detected responsive to average alpha power for a second epoch of time being elevated by a predetermined amount relative to average alpha power for a first immediately previous epoch of time. In some embodiments, the alpha rhythm is the most dominant detectable rhythm of the brain for sleep intention component 34. The alpha rhythm manifests in awake but relaxed individuals with their eyes closed. In some embodiments, sleep intention component 34 is configured to detect the alpha rhythm responsive to detecting oscillations of the EEG signals (and/or other signals output by sensor 18 and/or determined based on the information from sensor 18) between about 8 and 13 Hz with an amplitude between about 20 and 100 microvolts, for example.

Figure 2:
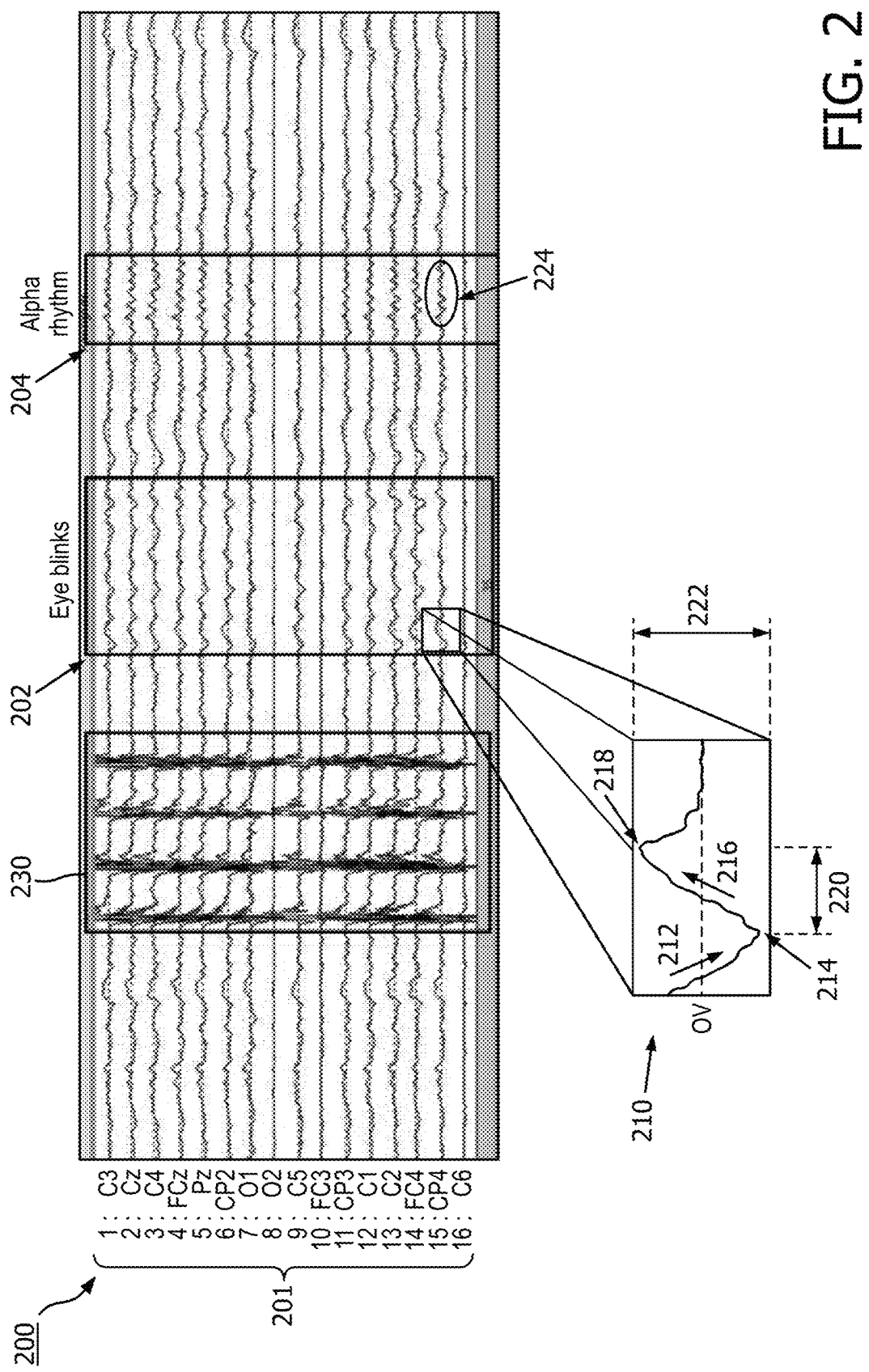
FIG. 2 illustrates an EEG signal for different locations on the scalp of the subject, in accordance with one or more embodiments.

By way of a non-limiting example, FIG. 2 illustrates an EEG signal 200 (e.g., determined by sleep stage component 30 using and/or based on the information in the output signals from sensor 18 shown in FIG. 1) for 16 different locations 201 (labeled 1-16 in FIG. 2) on the scalp of a subject (e.g., subject 12). Signal 200 shows eye blinks 202 and an alpha rhythm 204 in the signals from each location. For example, in the enlarged view of the portion of EEG signal 200 for location 15, signal 200 comprises a negative going zero crossing 212 to a negative peak 214, followed by a positive going zero crossing 216 and a positive peak 218, with a peak to peak distance 220 within a distance threshold range and a peak to peak amplitude 222 within an amplitude threshold range (e.g., determined by sleep intention component 34 shown in FIG. 1) This pattern is indicative of eye blinks as described above. FIG. 2 also shows oscillations 224 of the EEG signals between about 8 and 13 Hz with an amplitude between about 20 and 100 microvolts, for example, which are indicative of alpha rhythm 204. Finally, FIG. 2 illustrates a signal segment that is affected by artifacts 230.

Figure 3:
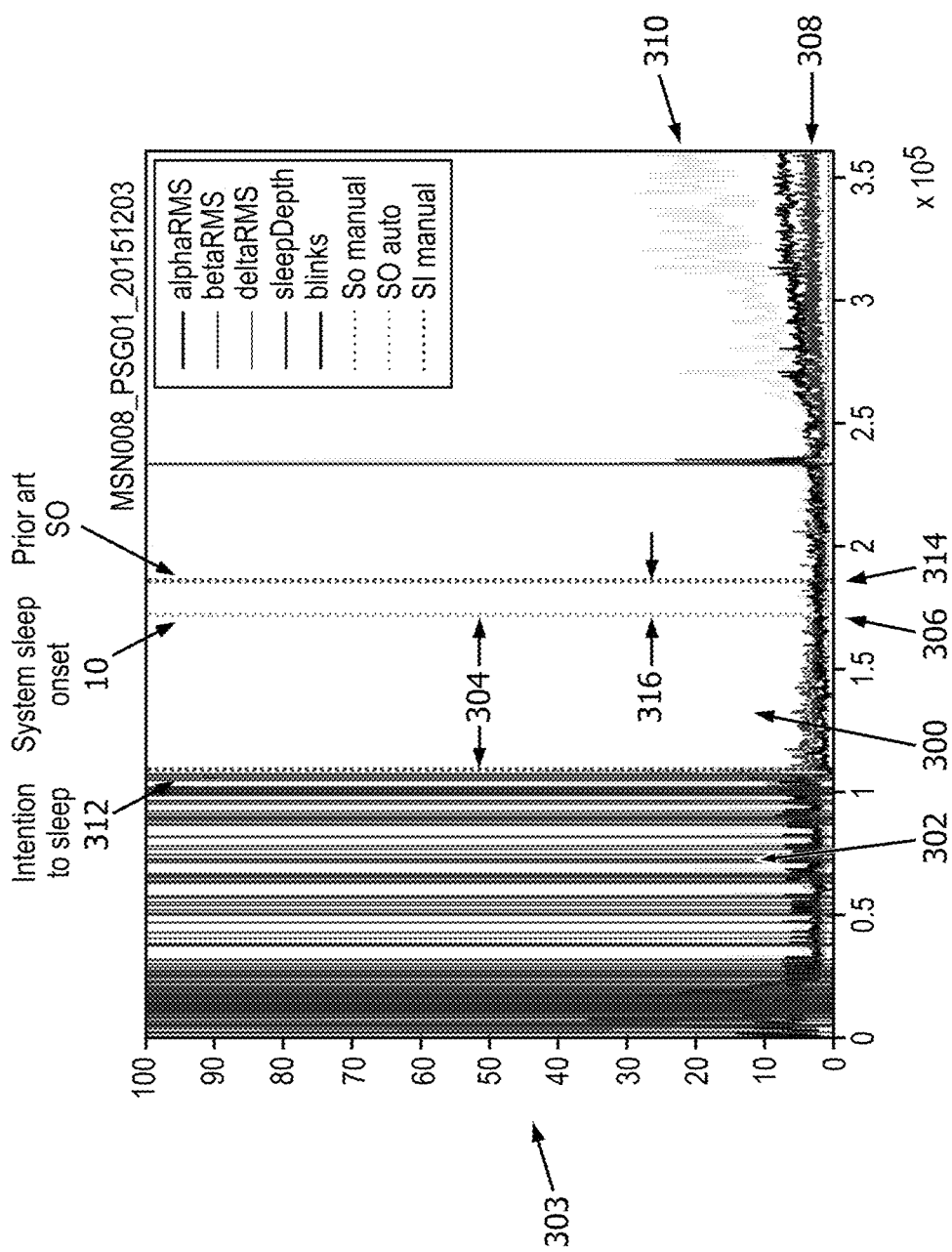
FIG. 3 illustrates various physiological events that occur and are detected by the system around the onset of sleep in the subject, in accordance with one or more embodiments.

FIG. 3 illustrates various physiological events that occur and are detected by system 10 (FIG. 1, as described above) around the onset of sleep. As shown in FIG. 3, a subject's intention to sleep 312 is evident when the subject stops blinking. For example, FIG. 3 illustrates the extinction 300 of eye blinks 302 a few minutes 304 before sleep onset 306. Eye blinks 302 are shown in FIG. 3 as detected variations in voltage 303. As shown in FIG. 3, the amplitude of a voltage change that corresponds to an eye blink is typically more than 100 microvolts. (It should be noted the lines in FIG. 3 indicate a moment an eye blink has been detected. This is not a physical eye-blink. It is a marker and/or a representation (e.g., a vertical line) that indicates a physical eye-blink). The power in the alpha band 308 also increases around sleep onset 306. Deeper stages of sleep, characterized by increased power in the delta band 310, are also present. Finally, FIG. 3 illustrates sleep onset 306 determined by system 10 as described above (e.g., based on determined sleep stage) compared to sleep onset 314 determined by a typical prior art system (e.g., based on lack of movement and/or sleep onset manually reported by a sleep technician scoring a particular recording, for example, as described above).

Returning to FIG. 1, as described above, sleep intention component 34 is configured to detect eye blinks and/or the alpha increase using thresholds related to the patterns described above. For example, for eye blink detection, sleep intention component 34 is configured to detect cosine waves (negative going zero crossing, negative peak, positive going zero crossing, positive peak) with peak to peak distance between about 100 and 500 milliseconds and an amplitude that breaches a predefined threshold such as about 100 microvolts. For alpha rhythm detection, sleep intention component 34 is configured to detect oscillations of the EEG signals between about 8 and 13 Hz with an amplitude between about 20 and 100 microvolts. The example thresholds and/or ranges described herein are not intended to be limiting. In some embodiments, sleep intention component 34 is configured such that the thresholds and/or information related to the thresholds is entered and/or selected by subject 12 and/or other users via user interface 24 and/or other devices, determined based on sensor 18 output signals and/or other information from a current and/or previous sleep sessions of subject 12, determined based on a type of sensor used as sensor 18, determined based on information in external resources 26 and/or electronic storage 22, and/or is determined by other methods.

For example, an individual threshold may be adjusted by sleep intention component 34 based on a type of EEG acquisition system and/or electrodes (sensor 18) used. Dry electrodes may cause differences in signal amplitudes compared to wet electrodes. In some embodiments, a type of a particular threshold may be adjusted. For example, sleep intention component 34 may be configured such that sleep intention is detected and the sleep intention moment is determined responsive to a number of eye blinks being within a maximum blinks allowed threshold range in a given epoch of time, instead of responsive to a complete cessation of blinking. As another example, sleep intention component 34 may be configured such that sleep intention is detected and the sleep intention moment is determined responsive to changes in the ratio of mean power in the alpha frequency band while the eyes of subject 12 are closed relative to the mean alpha power during while the eyes of subject 12 are open (the alpha attenuation coefficient). In some embodiments, the alpha attenuation coefficient is determined by sleep intention component 34 and used to detect the closing of the eyes of subject 12 using information conveyed by the sensor 18 output signals over two or more consecutive epochs of time. In some embodiments, sleep intention component 34 is configured such that, responsive to the alpha attenuation coefficient exceeding a predefined value, the eyes of subject 12 are determined to be closed in a most recent epoch used to determine the alpha attenuation coefficient. The alpha attenuation coefficient typically ranges between 0.8 and 3. Sleep intention component 34 is configured to determine that the eyes of subject 12 are closed responsive to the alpha attenuation coefficient for subject 12 breaching a value of about 1.5-1.8 (this is an example only), and/or other values. This example value is not intended to be limiting and may depend on a type of sensor, a type of EEG (system), and/or other characteristics of system 10.

In some embodiments, sleep intention component 34 is configured to use machine learning algorithms to create one or more classifiers configured to distinguish between periods when the eyes of subject 12 are open versus periods when the eyes of subject 12 are closed. In some embodiments, a classifier is a mathematical function (implemented through regression models or neural networks) optimized to identify to which class (e.g., eyes open or eyes closed) a new epoch belongs to on the basis of a training set containing examples of the above described events. In some embodiments, sleep intention component 34 is configured such that the classifiers are trained on the raw signals and/or relevant features are extracted to separate the two classes (e.g., eyes open or eyes closed).

Sleep onset latency component 36 is configured to determine sleep onset latency for subject 12. The sleep onset latency is determined based on the sleep onset moment, the sleep intention moment, and/or other information. In some embodiments, sleep onset latency component 36 is configured to determine sleep onset latency for subject 12 using Equation 1 described above. According to Equation 1, sleep onset latency is the time difference between the sleep intention moment for subject 12 (e.g., the time at which subject 12 decides to initiate sleep) and the sleep onset moment for subject 12 (the time at which subject 12 actually falls asleep).

Figure 4:
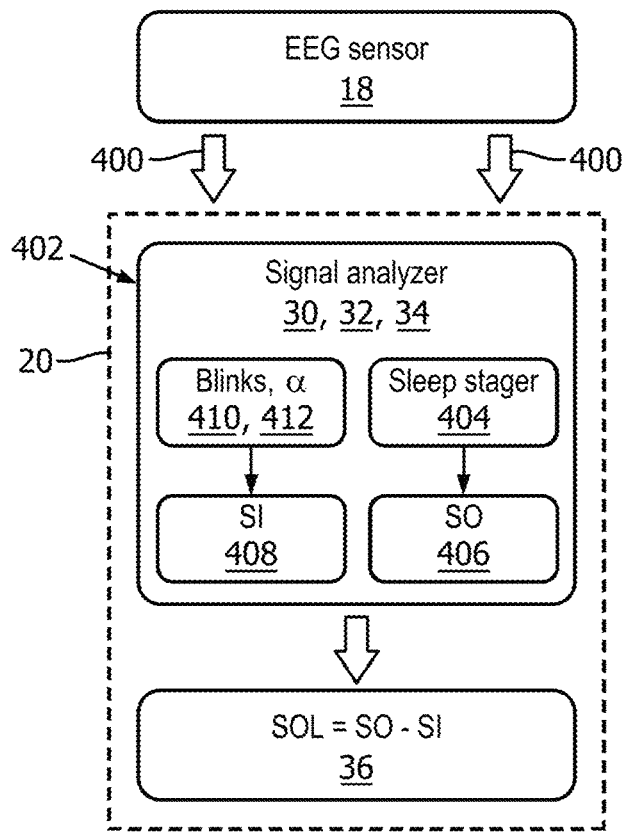
FIG. 4 is a schematic illustration of the determination of sleep onset latency by the system, in accordance with one or more embodiments.

FIG. 4 is a schematic illustration of the determination of sleep onset latency by sleep onset latency component 36 (FIG. 1). As shown in FIG. 4, EEG sensor(s) 18 generates output signals 400 conveying information related to brain activity in a subject (e.g., subject 12 shown in FIG. 1) during a sleep session. One or more hardware processors 20 are operatively coupled with the sensors 18. One or more hardware processors 20 include sleep stage component 30, sleep onset component 32, sleep intention component 34, and sleep onset latency component 36. FIG. 4 illustrates components 30-34 formed together as a signal analyzer 402. Signal analyzer 402 (e.g., sleep stage component 30) is configured to determine sleep stages 404 of the subject based on output signals 400. Signal analyzer 402 is configured to determine a sleep onset moment 406 in the subject based on the determined sleep stages 404. Signal analyzer 402 is configured to determine a sleep intention moment 408 for the subject. The sleep intention moment is determined by: detecting eye blinks 410 in the subject based on the output signals, and determining the sleep intention moment responsive to the detected eye blinks ceasing for a predetermined period of time; or determining 412 whether brain activity power (e.g., alpha power) in a target frequency band has breached a threshold power level based on the output signals, and determining the sleep intention moment responsive to a breach; or a combination of 410 and 412. Sleep onset latency component 36 is configured to determine the sleep onset latency based on the sleep onset moment 406 and the sleep intention moment 408 (e.g., according to Equation 1 described above).

Returning to FIG. 1, in some embodiments, control component 38 is configured to control one or more stimulators 16 to provide stimulation to subject 12 during sleep sessions and/or at other times. In some embodiments, stimulators 16 are controlled to provide stimulation according to a predetermined therapy regime based on the output signals, the sleep onset latency determination, and/or other information. Sleep slow waves can be enhanced through (e.g. peripheral auditory, magnetic, electrical, and/or other) stimulation delivered in NREM sleep. Control component 38 (and/or other processor components) monitors the brain activity of subject 12 based on the output signals of sensors 18 (e.g., based on an EEG), the sleep onset latency determination, and/or other information during sleep sessions and controls the delivery of stimulation (e.g., auditory and/or other stimulation) by stimulator 16 to control SWA in subject 12. In some embodiments, based on the output signals, the sleep onset latency determination, and/or other information, control component 30 (and/or one or more of the other processor components described below) performs one or more operations similar to and/or the same as the operations described in U.S. patent application Ser. No. 14/784,782 (entitled "System and Method for Sleep Session Management Based on Slow Wave Sleep Activity in a Subject"), Ser. No. 14/783,114 (entitled "System and Method for Enhancing Sleep Slow Wave Activity Based on Cardiac Activity"), Ser. No. 14/784,746 (entitled "Adjustment of Sensory Stimulation Intensity to Enhance Sleep Slow Wave Activity"), Ser. No. 15/101,008 (entitled "System and Method for Determining Sleep Stage Based on Sleep Cycle"), and/or Ser. No. 15/100,435 (entitled "System and Method for Facilitating Sleep Stage Transitions"), which are all individually incorporated by reference in their entireties.

Sensory stimulator 16 is configured to facilitate transitions between sleep stages, maintain sleep in a specific stage, and/or perform other operations through non-invasive brain stimulation and/or other methods. Sensory stimulator 16 may be configured to facilitate transitions between sleep stages, maintain sleep in a specific stage, and/or perform other operations through non-invasive brain stimulation using auditory, electric, magnetic, visual, somatosensory, and/or other sensory stimuli. The auditory, electric, magnetic, visual, somatosensory, and/or other sensory stimulation may include auditory stimulation, visual stimulation, somatosensory stimulation, electrical stimulation, magnetic stimulation, a combination of different types of stimulation, and/or other stimulation. The auditory, electric, magnetic, visual, somatosensory, and/or other sensory stimuli include odors, sounds, visual stimulation, touches, tastes, somatosensory stimulation, haptic, electrical, magnetic, and/or other stimuli. For example, acoustic tones may be provided to subject 12 to enhance slow wave sleep in subject 12. Examples of sensory stimulator 16 may include one or more of a sound generator, a speaker, a music player, a tone generator, one or more electrodes on the scalp of subject 12, a vibrator (such as a piezoelectric member, for example) to deliver vibratory stimulation, a coil generating a magnetic field to directly stimulate the brain's cortex, one or more light generators or lamps, a fragrance dispenser, and/or other devices. In some embodiments, sensory stimulator 16 is configured to adjust the intensity, timing, and/or other parameters of the stimulation provided to subject 12 (e.g., as described herein).

Electronic storage 22 comprises electronic storage media that electronically stores information. The electronic storage media of electronic storage 22 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 22 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), cloud storage, and/or other electronically readable storage media. Electronic storage 22 may store software algorithms, information determined by processor 20, information received via user interface 24 and/or external computing systems (e.g., external resources 26), and/or other information that enables system 10 to function as described herein. Electronic storage 22 may be (in whole or in part) a separate component within system 10, or electronic storage 22 may be provided (in whole or in part) integrally with one or more other components of system 10 (e.g., processor 20).

User interface 24 is configured to provide an interface between system 10 and subject 12, and/or other users through which subject 12 and/or other users may provide information to and receive information from system 10. This enables data, cues, results, and/or instructions and any other communicable items, collectively referred to as "information," to be communicated between a user (e.g., subject 12) and one or more of sensory stimulator 16, sensor 18, processor 20, and/or other components of system 10. For example, an EEG, a sleep onset latency value, and/or other information may be displayed to a caregiver via user interface 24. As another example, user interface 24 may be and/or be included in a computing device such as a desktop computer, a laptop computer, a smartphone, a tablet computer, and/or other computing devices. Such computing devices may run one or more electronic applications having graphical user interfaces configured to provide information to and/or receive information from users.

Examples of interface devices suitable for inclusion in user interface 24 comprise a keypad, buttons, switches, a keyboard, knobs, levers, a display screen, a touch screen, speakers, a microphone, an indicator light, an audible alarm, a printer, a tactile feedback device, and/or other interface devices. In some embodiments, user interface 24 comprises a plurality of separate interfaces. In some embodiments, user interface 24 comprises at least one interface that is provided integrally with processor 20 and/or other components of system 10. In some embodiments, user interface 24 is configured to communicate wirelessly with processor 20 and/or other components of system 10.

It is to be understood that other communication techniques, either hard-wired or wireless, are also contemplated by the present disclosure as user interface 24. For example, the present disclosure contemplates that user interface 24 may be integrated with a removable storage interface provided by electronic storage 22. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 24 comprise, but are not limited to, an RS-232 port, RF link, an IR link, modem (telephone, cable or other). In short, any technique for communicating information with system 10 is contemplated by the present disclosure as user interface 24.

External resources 26 include sources of information (e.g., databases, websites, etc.), external entities participating with system 10 (e.g., a medical records system of a health care provider), medical and/or other equipment (e.g., lamps and/or other lighting devices, sound systems, audio and/or visual recording devices, etc.) configured to communicate with and/or be controlled by system 10, one or more servers outside of system 10, a network (e.g., the internet), electronic storage, equipment related to Wi-Fi technology, equipment related to Bluetooth® technology, data entry devices, sensors, scanners, computing devices associated with individual users, and/or other resources. In some implementations, some or all of the functionality attributed herein to external resources 26 may be provided by resources included in system 10. External resources 26 may be configured to communicate with processor 20, user interface 24, sensor 18, electronic storage 22, sensory stimulator 16, and/or other components of system 10 via wired and/or wireless connections, via a network (e.g., a local area network and/or the internet), via cellular technology, via Wi-Fi technology, and/or via other resources.

Figure 5:
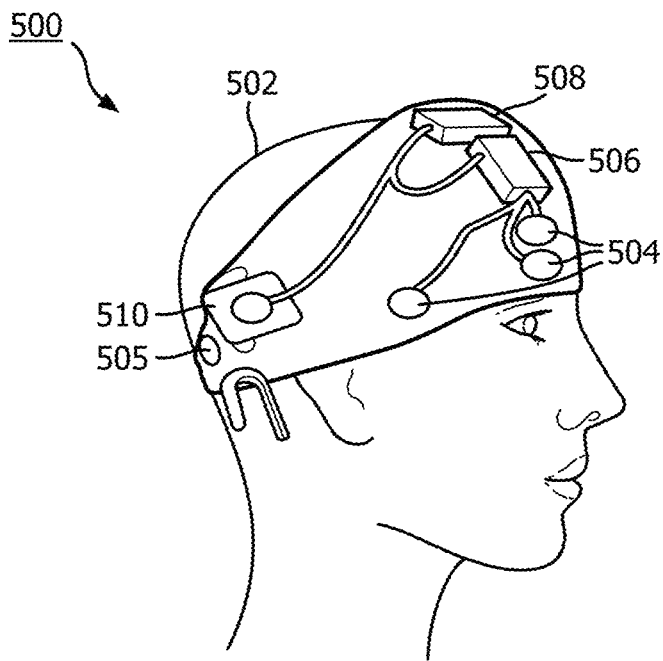
FIG. 5 illustrates a headset worn by the subject, in accordance with one or more embodiments.

In FIG. 1, sensory stimulator 16, sensor 18, processor 20, electronic storage 22, and user interface 24 are shown as separate entities. This is not intended to be limiting. Some and/or all of the components of system 10 and/or other components may be grouped into one or more singular devices. For example, FIG. 5 illustrates a headset 500 worn by a subject 502 (e.g., subject 12 shown in FIG. 1). Headset 500 includes sensing electrodes 504, a reference electrode 505, one or more devices associated with an EEG 506, means to deliver auditory stimulation (e.g., a wired and/or wireless audio device and/or other devices) 508, and one or more audio speakers 510. Audio speakers 510 may be located in and/or near the ears of subject 502 and/or in other locations. The reference electrode 505 may be located behind the ear of subject 502, and/or in other locations. In the example shown in FIG. 5, sensing electrodes 504 may be configured to generate output signals conveying information related to brain activity of subject 502, and/or other information. The output signals may be transmitted to a processor (e.g., processor 20 shown in FIG. 1), a computing device (e.g., a bedside laptop) which may or may not include the processor, and/or other devices wirelessly and/or via wires. Acoustic stimulation may be delivered to subject 502 via wireless audio device 508 and/or speakers 510. Sensing electrodes 504, reference electrode 505, and devices 506 may be represented, for example, by sensor 18 in FIG. 1. Wireless audio device 508 and speakers 510 may be represented, for example, by sensory stimulator 16 shown in FIG. 1. In this example, a computing device (not shown in FIG. 5) may include processor 20, electronic storage 22, user interface 24, and/or other components of system 10 shown in FIG. 1.

Figure 6:
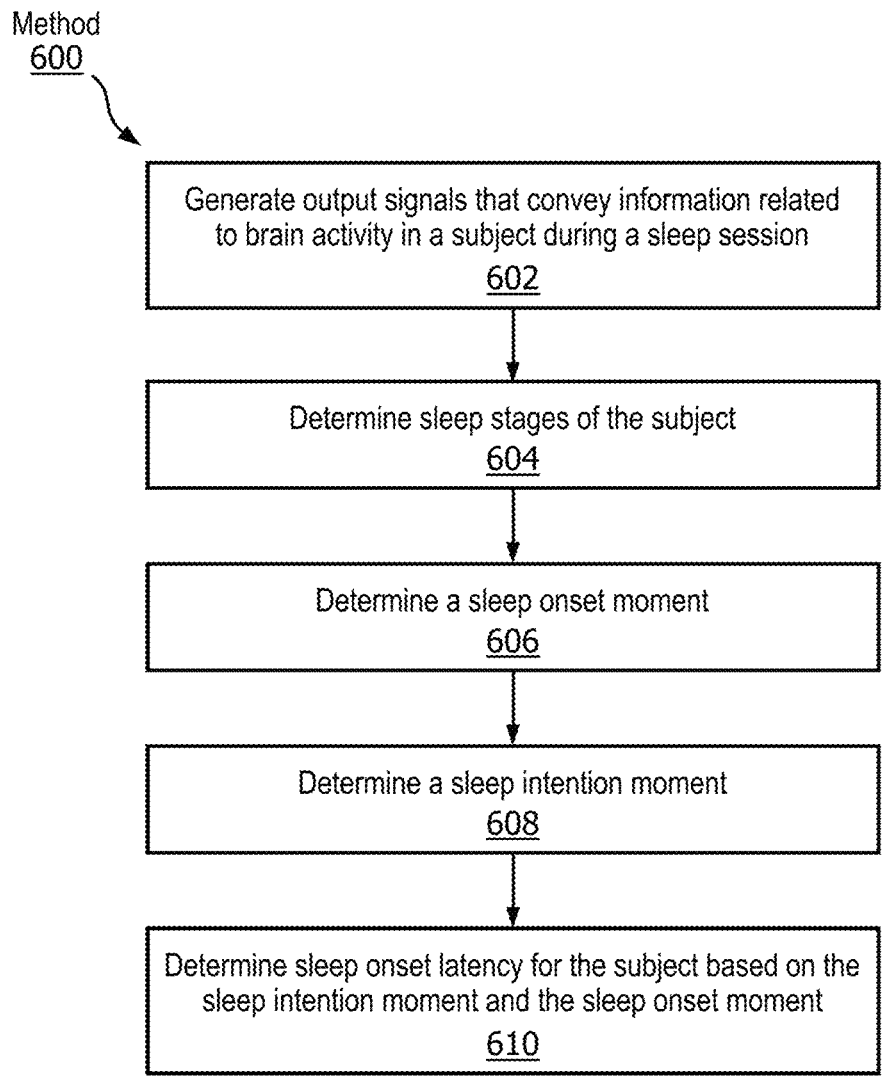
FIG. 6 illustrates a method for determining sleep onset latency in the subject for a sleep session, in accordance with one or more embodiments.

FIG. 6 illustrates method 600 for determining sleep onset latency in a subject for a sleep session with a determination system. The system comprises one or more sensors, one or more hardware processors configured by machine readable instructions, and/or other components. The hardware processors are configured to execute computer program components. The computer program components comprise a sleep stage component, a sleep onset component, a sleep intention component, a sleep onset latency component, a control component, and/or other components. The operations of method 600 presented below are intended to be illustrative. In some embodiments, method 600 may be accomplished with one or more additional operations not described, and/or without one or more of the operations discussed. Additionally, the order in which the operations of method 600 are illustrated in FIG. 6 and described below is not intended to be limiting. For example, in a system operating in real-time, sleep intention (e.g., operation 608 described below) may be detected before sleep onset (e.g., operation 606 described below). SOL may then be determined as the difference between SO and SI as described in Equation 1 above, and/or by a counter/buffer accumulating samples from the moment SI is detected until SO is detected.

In some embodiments, method 600 may be implemented in one or more processing devices (e.g., a digital processor, an analog processor, a digital circuit designed to process information, an analog circuit designed to process information, a state machine, and/or other mechanisms for electronically processing information). The processing devices may include one or more devices executing some or all of the operations of method 600 in response to instructions stored electronically on an electronic storage medium. The processing devices may include one or more devices configured through hardware, firmware, and/or software to be specifically designed for execution of one or more of the operations of method 600.

At an operation 602, output signals conveying information related to brain activity in the subject are generated. In some embodiments, the sensors comprise electroencephalogram (EEG) sensors and/or other sensors configured to generate output signals conveying information related to slow wave activity in the subject. In some embodiments, the sensors comprise one or more of an EEG electrode, an electrooculogram (EOG) electrode, an actigraphy sensor, an electrocardiogram (EKG) electrode, a respiration sensor, a pressure sensor, a vital signs camera, a photoplethysmogram (PPG) sensor, or a functional near infra-red sensor (fNIR). In some embodiments, operation 602 is performed by one or more sensors the same as or similar to sensors 18 (shown in FIG. 1 and described herein).

At an operation 604, sleep stages of the subject are determined. The sleep stages indicate presence of sleep in the subject during the sleep session. In some embodiments, operation 604 is performed by a processor component the same as or similar to sleep stage component 30 (shown in FIG. 1 and described herein).

At an operation 606, a sleep onset moment of the subject is determined. The sleep onset moment comprises a moment in time indicating a start of sleep in the subject during the sleep session. In some embodiments, determining the sleep onset moment in the subject comprises determining whether the subject has spent a predetermined amount of time in a predetermined sleep stage, and responsive to the subject spending the predetermined amount of time in the predetermined sleep stage, determining the sleep onset moment as a starting time of the predetermined amount of time in the predetermined sleep stage. In some embodiments, operation 606 is performed by a processor component the same as or similar to sleep onset component 32 (shown in FIG. 1 and described herein).

At an operation 608, a sleep intention moment is determined for the subject. The sleep intention moment comprises a moment in time indicating an intention of the subject to initiate sleep. The sleep intention moment is determined by: (i) detecting eye blinks in the subject based on the output signals, and determining the sleep intention moment responsive to the detected eye blinks ceasing for a predetermined period of time; or (ii) determining whether brain activity power in a target frequency band has breached a threshold power level based on the output signals, and determining the sleep intention moment responsive to a breach; or (iii) a combination of (i) and (ii). In some embodiments, detecting eye blinks in the subject comprises detecting a negative going zero crossing to a negative peak for a voltage of the output signals, followed by a positive going zero crossing and a positive peak, with a peak to peak distance within a distance threshold range and a peak to peak amplitude within an amplitude threshold range. In some embodiments, with respect to determining whether the brain activity power in the target frequency band has breached the threshold power level, the power is the alpha power, the target frequency band is the 8-13 Hz frequency band, the threshold power level is an average alpha power level; and a breach is detected responsive to average alpha power for a second epoch of time being elevated by a predetermined amount relative to average alpha power for a first immediately previous epoch of time. In some embodiments, operation 608 is performed by a processor component the same as or similar to sleep intention component 34 (shown in FIG. 1 and described herein).

At an operation 610, sleep onset latency is determined for the subject. The sleep onset latency is determined based on the sleep onset moment and the sleep intention moment. In some embodiments, operation 610 is performed by a processor component the same as or similar to sleep onset latency component 36 (shown in FIG. 1 and described herein).

In some embodiments, the system further comprises one or more sensory stimulators configured to provide sensory stimulation to the subject. In these embodiments, the method further comprises controlling the sensory stimulators with the hardware processors based on the output signals to induce and/or enhance sleep in the subject during the sleep session. In some embodiments, this operation is performed by a processor component the same as or similar to control component 38 (shown in FIG. 1 and described herein)

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination

What is claimed is:

1. A system configured to determine sleep onset latency for a subject for a sleep session, the system comprising:
    one or more sensors configured to generate output signals conveying information related to brain activity in the subject during the sleep session; and
    one or more hardware processors operatively coupled with the one or more sensors, the one or more hardware processors configured by machine-readable instructions to:
    determine one or more sleep stages of the subject based on the output signals, the one or more sleep stages indicating presence of sleep in the subject during the sleep session;
    determine a sleep onset moment in the subject based on the one or more sleep stages, the sleep onset moment comprising a moment in time indicating a start of sleep in the subject during the sleep session;
    determine a sleep intention moment for the subject, the sleep intention moment comprising a moment in time indicating an intention of the subject to initiate sleep, the sleep intention moment determined by:
    (i) detecting eye blinks in the subject based on the output signals, and determining the sleep intention moment responsive to the detected eye blinks ceasing for a predetermined period of time; and
    (ii) determining whether brain activity power in a target frequency band has breached a threshold power level based on the output signals, and determining the sleep intention moment responsive to a breach; and
    determine the sleep onset latency based on the sleep onset moment and the sleep intention moment.

2. The system of claim 1, wherein the one or more hardware processors are configured such that determining the sleep intention moment for the subject includes detecting eye blinks in the subject, and wherein detecting eye blinks in the subject comprises detecting a negative going zero crossing to a negative peak for a voltage of the output signals, followed by a positive going zero crossing and a positive peak, with a peak to peak distance within a distance threshold range and a peak to peak amplitude within an amplitude threshold range.

3. The system of claim 1, wherein the one or more hardware processors are configured such that determining the sleep onset moment in the subject comprises determining whether the subject has spent a predetermined amount of time in a predetermined sleep stage, and responsive to the subject spending the predetermined amount of time in the predetermined sleep stage, determining the sleep onset moment as a starting time of the predetermined amount of time in the predetermined sleep stage.

4. The system of claim 1, further comprising one or more sensory stimulators configured to provide sensory stimulation to the subject, the one or more sensory stimulators controlled by the one or more hardware processors based on the output signals and the sleep onset latency to induce and/or enhance sleep in the subject during the sleep session.

5. A system configured to determine sleep onset latency for a subject for a sleep session, the system comprising:
    one or more sensors configured to generate output signals conveying information related to brain activity in the subject during the sleep session; and
    one or more hardware processors operatively coupled with the one or more sensors, the one or more hardware processors configured by machine-readable instructions to:
    determine one or more sleep stages of the subject based on the output signals, the one or more sleep stages indicating presence of sleep in the subject during the sleep session;
    determine a sleep onset moment in the subject based on the one or more sleep stages, the sleep onset moment comprising a moment in time indicating a start of sleep in the subject during the sleep session;
    determine a sleep intention moment for the subject, the sleep intention moment comprising a moment in time indicating an intention of the subject to initiate sleep, the sleep intention moment determined by:
    (i) detecting eye blinks in the subject based on the output signals, and determining the sleep intention moment responsive to the detected eye blinks ceasing for a predetermined period of time; or
    (ii) determining whether brain activity power in a target frequency band has breached a threshold power level based on the output signals, and determining the sleep intention moment responsive to a breach; or
    (iii) a combination of (i) and (ii); and determine the sleep onset latency based on the sleep onset moment and the sleep intention moment;

wherein the one or more hardware processors are configured such that determining the sleep intention moment for the subject includes determining whether the brain activity power in the target frequency band has breached the threshold power level, wherein:

the power is alpha power;

the target frequency band is the 8-13 Hz frequency band;

the threshold power level is an average alpha power level; and the breach is detected responsive to average alpha power for a second epoch of time being elevated by a predetermined amount relative to average alpha power for a first immediately previous epoch of time.

6. A system configured to determine sleep onset latency for a subject for a sleep session, the system comprising:

one or more sensors configured to generate output signals conveying information related to brain activity in the subject during the sleep session;

one or more sensory stimulators configured to provide sensory stimulation to the subject, the one or more sensory stimulators controlled by one or more hardware processors based on the output signals and the sleep onset latency to induce and/or enhance sleep in the subject during the sleep session; and the one or more hardware processors operatively coupled with the one or more sensors, the one or more hardware processors configured by machine-readable instructions to:

determine one or more sleep stages of the subject based on the output signals, the one or more sleep stages indicating presence of sleep in the subject during the sleep session;

determine a sleep onset moment in the subject based on the one or more sleep stages, the sleep onset moment comprising a moment in time indicating a start of sleep in the subject during the sleep session;

determine a sleep intention moment for the subject, the sleep intention moment comprising a moment in time indicating an intention of the subject to initiate sleep, the sleep intention moment determined by:
  (i) detecting eye blinks in the subject based on the output signals, and determining the sleep intention moment responsive to the detected eye blinks ceasing for a predetermined period of time; or
  (ii) determining whether brain activity power in a target frequency band has breached a threshold power level based on the output signals, and determining the sleep intention moment responsive to a breach; or
  (iii) a combination of (i) and (ii); and determine the sleep onset latency based on the sleep onset moment and the sleep intention moment;

wherein one or more of the one or more sensors, the one or more hardware processors, and the one or more sensory stimulators are included in a garment configured to be worn by the subject, and wherein the one or more hardware processors are configured to cause display of the sleep onset latency on a computing device associated with the subject.

7. A method for determining sleep onset latency for a subject for a sleep session with a determination system, the system comprising one or more sensors and one or more hardware processors, the method comprising:

generating, with the one or more sensors, output signals conveying information related to brain activity in the subject during the sleep session;

determining, with the one or more hardware processors, one or more sleep stages of the subject based on the output signals, the one or more sleep stages indicating presence of sleep in the subject during the sleep session;

determining, with the one or more hardware processors, a sleep onset moment in the subject based on the one or more sleep stages, the sleep onset moment comprising a moment in time indicating a start of sleep in the subject during the sleep session;

determining, with the one or more hardware processors, a sleep intention moment for the subject, the sleep intention moment comprising a moment in time indicating an intention of the subject to initiate sleep, the sleep intention moment determined by:
  (i) detecting eye blinks in the subject based on the output signals, and determining the sleep intention moment responsive to the detected eye blinks ceasing for a predetermined period of time; and
  (ii) determining whether brain activity power in a target frequency band has breached a threshold power level based on the output signals, and determining the sleep intention moment responsive to a breach; and determining, with the one or more hardware processors, the sleep onset latency based on the sleep onset moment and the sleep intention moment.

8. The method of claim 7, wherein determining the sleep intention moment for the subject includes detecting eye blinks in the subject, and wherein detecting eye blinks in the subject comprises detecting a negative going zero crossing to a negative peak for a voltage of the output signals, followed by a positive going zero crossing and a positive peak, with a peak to peak distance within a distance threshold range and a peak to peak amplitude within an amplitude threshold range.

9. The method of claim 7, wherein determining the sleep onset moment in the subject comprises determining whether the subject has spent a predetermined amount of time in a predetermined sleep stage, and responsive to the subject spending the predetermined amount of time in the predetermined sleep stage, determining the sleep onset moment as a starting time of the predetermined amount of time in the predetermined sleep stage.

10. The method of claim 7, wherein the system further comprises one or more sensory stimulators configured to provide sensory stimulation to the subject, the method further comprising controlling the one or more sensory stimulators with the one or more hardware processors based on the output signals and the sleep onset latency to induce and/or enhance sleep in the subject during the sleep session.

11. A method for determining sleep onset latency for a subject for a sleep session with a determination system, the system comprising one or more sensors and one or more hardware processors, the method comprising:

generating, with the one or more sensors, output signals conveying information related to brain activity in the subject during the sleep session;

determining, with the one or more hardware processors, one or more sleep stages of the subject based on the output signals, the one or more sleep stages indicating presence of sleep in the subject during the sleep session;

determining, with the one or more hardware processors, a sleep onset moment in the subject based on the one or more sleep stages, the sleep onset moment comprising a moment in time indicating a start of sleep in the subject during the sleep session;

determining, with the one or more hardware processors, a sleep intention moment for the subject, the sleep intention moment comprising a moment in time indicating an intention of the subject to initiate sleep, the sleep intention moment determined by:
  (i) detecting eye blinks in the subject based on the output signals, and determining the sleep intention moment responsive to the detected eye blinks ceasing for a predetermined period of time; or
  (ii) determining whether brain activity power in a target frequency band has breached a threshold power level based on the output signals, and determining the sleep intention moment responsive to a breach; or
  (iii) combination of (i) and (ii); and
determining, with the one or more hardware processors, the sleep onset latency based on the sleep onset moment and the sleep intention moment;
wherein determining the sleep intention moment for the subject includes determining whether the brain activity power in the target frequency band has breached the threshold power level, wherein:
  the power is alpha power;
  the target frequency band is the 8-13 Hz frequency band;
  the threshold power level is an average alpha power level; and
  the breach is detected responsive to average alpha power for a second epoch of time being elevated by a predetermined amount relative to average alpha power for a first immediately previous epoch of time.

12. A method for determining sleep onset latency for a subject for a sleep session with a determination system, the system comprising one or more sensors, one or more sensory stimulators configured to provide sensory stimulation to the subject, and one or more hardware processors, the method comprising:
  generating, with the one or more sensors, output signals conveying information related to brain activity in the subject during the sleep session;
  determining, with the one or more hardware processors, one or more sleep stages of the subject based on the output signals, the one or more sleep stages indicating presence of sleep in the subject during the sleep session;
  determining, with the one or more hardware processors, a sleep onset moment in the subject based on the one or more sleep stages, the sleep onset moment comprising a moment in time indicating a start of sleep in the subject during the sleep session;
  determining, with the one or more hardware processors, a sleep intention moment for the subject, the sleep intention moment comprising a moment in time indicating an intention of the subject to initiate sleep, the sleep intention moment determined by:
    (i) detecting eye blinks in the subject based on the output signals, and determining the sleep intention moment responsive to the detected eye blinks ceasing for a predetermined period of time; or
    (ii) determining whether brain activity power in a target frequency band has breached a threshold power level based on the output signals, and determining the sleep intention moment responsive to a breach; or
    (iii) combination of (i) and (ii); and
  determining, with the one or more hardware processors, the sleep onset latency based on the sleep onset moment and the sleep intention moment;
  controlling the one or more sensory stimulators with the one or more hardware processors based on the output signals and the sleep onset latency to induce and/or enhance sleep in the subject during the sleep session; and
wherein one or more of the one or more sensors, the one or more hardware processors, and the one or more sensory stimulators are included in a garment configured to be worn by the subject, and wherein the method further comprises causing display, with the one or more hardware processors, of the sleep onset latency on a computing device associated with the subject.

* * * * *